(12) United States Patent
Kabumoto et al.

(10) Patent No.: US 7,980,760 B2
(45) Date of Patent: Jul. 19, 2011

(54) X-RAY INSPECTION APPARATUS AND X-RAY INSPECTION PROGRAM

(75) Inventors: Takashi Kabumoto, Shiga (JP); Atsushi Iwai, Shiga (JP)

(73) Assignee: Ishida Co., Ltd., Kyoto (JP)

( * ) Notice: Subject to any disclaimer, the term of this patent is extended or adjusted under 35 U.S.C. 154(b) by 255 days.

(21) Appl. No.: 12/374,573

(22) PCT Filed: Jul. 12, 2007

(86) PCT No.: PCT/JP2007/063911
§ 371 (c)(1),
(2), (4) Date: Jan. 21, 2009

(87) PCT Pub. No.: WO2008/013063
PCT Pub. Date: Jan. 31, 2008

(65) Prior Publication Data
US 2010/0002835 A1    Jan. 7, 2010

(30) Foreign Application Priority Data

Jul. 24, 2006  (JP) ................................. 2006-200283

(51) Int. Cl.
*G01D 18/00* (2006.01)
(52) U.S. Cl. .............................. 378/207; 378/57; 378/62

(58) Field of Classification Search .................... 378/51, 378/57, 58, 62, 207
See application file for complete search history.

(56) References Cited

FOREIGN PATENT DOCUMENTS

| JP | H03-116299 A | 5/1991 |
|---|---|---|
| JP | H10-339707 A | 12/1998 |
| JP | 2001-004560 A | 1/2001 |
| JP | 2005-091016 A | 4/2005 |
| JP | 2005-351794 A | 12/2005 |
| JP | 2006-071423 A | 3/2006 |
| JP | 2006-170652 A | 6/2006 |

*Primary Examiner* — Jurie Yun
(74) *Attorney, Agent, or Firm* — Global IP Counselors, LLP

(57) ABSTRACT

An X-ray inspection apparatus detects, by an X-ray line sensor, X-rays irradiated towards a product placed on a conveyor and transmitted therethrough in order to detect the presence of foreign matter contained in the product. The X-ray inspection apparatus includes a determination unit and a calibrating unit. The determination unit is configured to determine, based on detection results by a line sensor obtained at each of prescribed positions of the conveyor, whether each of the prescribed positions of the conveyor is an appropriate position for calibrating the line sensor. The calibrating unit is configured to calibrate the line sensor based on detection results obtained by the line sensor at a position that is determined by the determination unit to be the appropriate position for calibrating the line sensor.

9 Claims, 12 Drawing Sheets

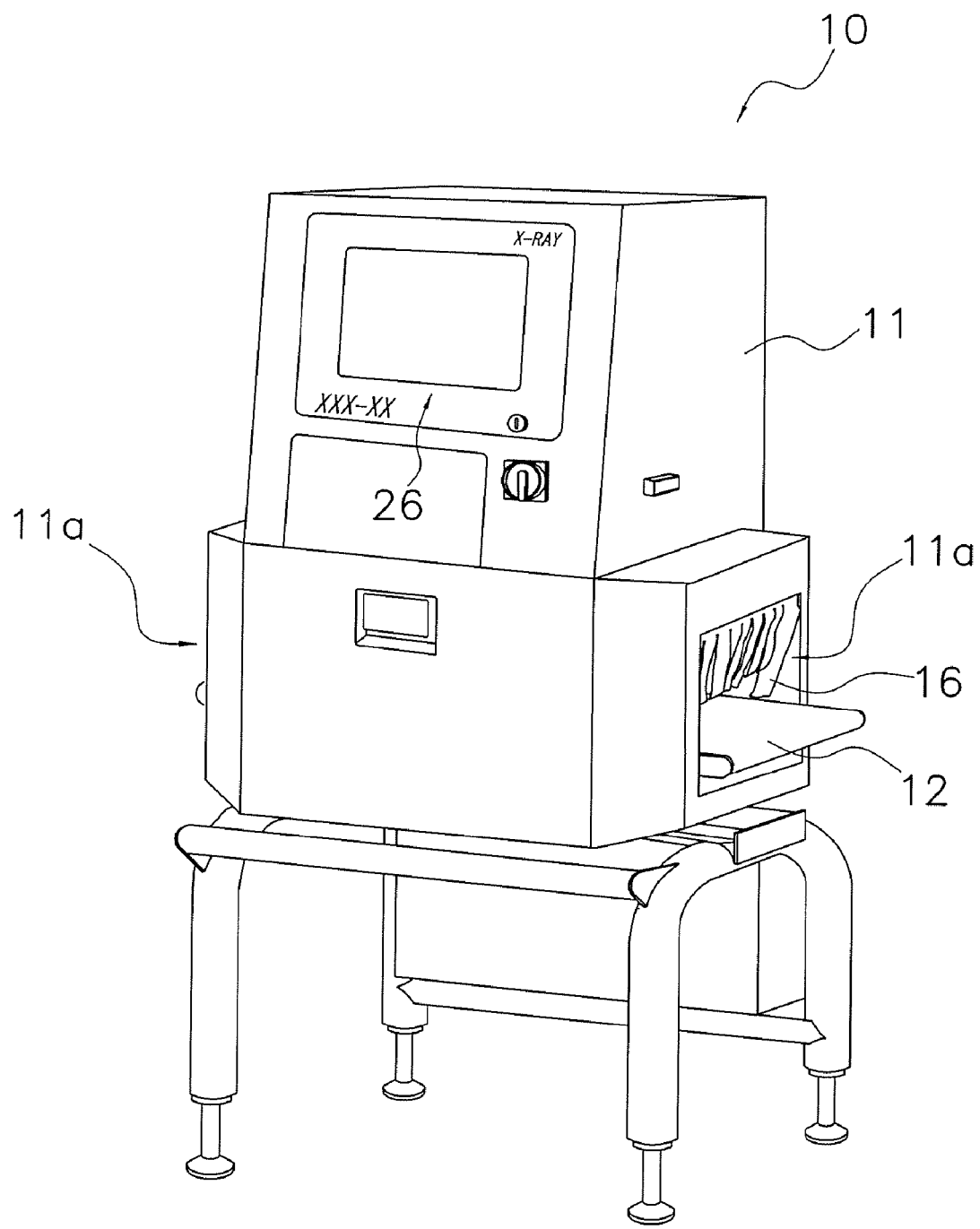
F I G. 1

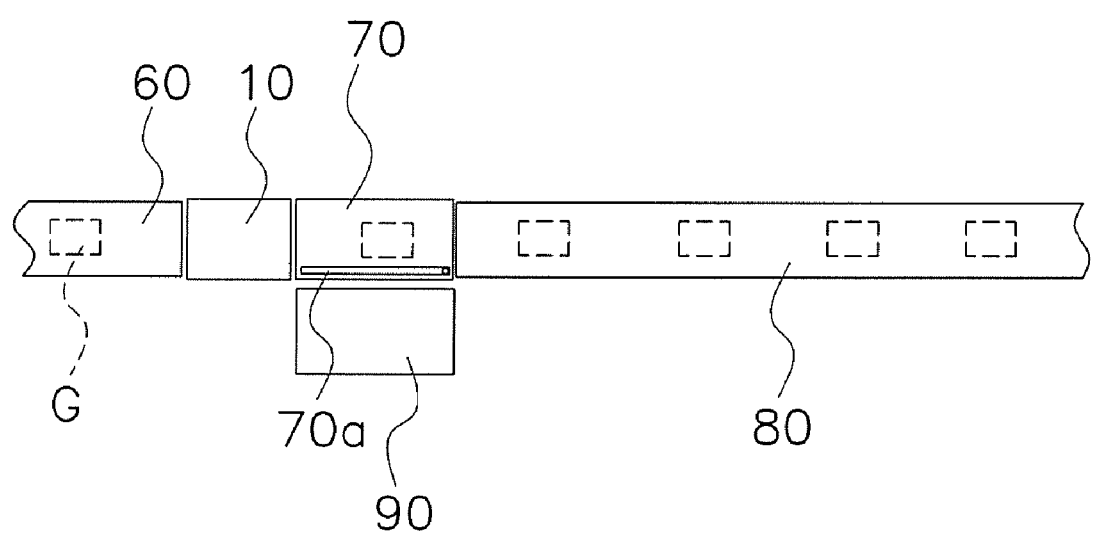
F I G. 2

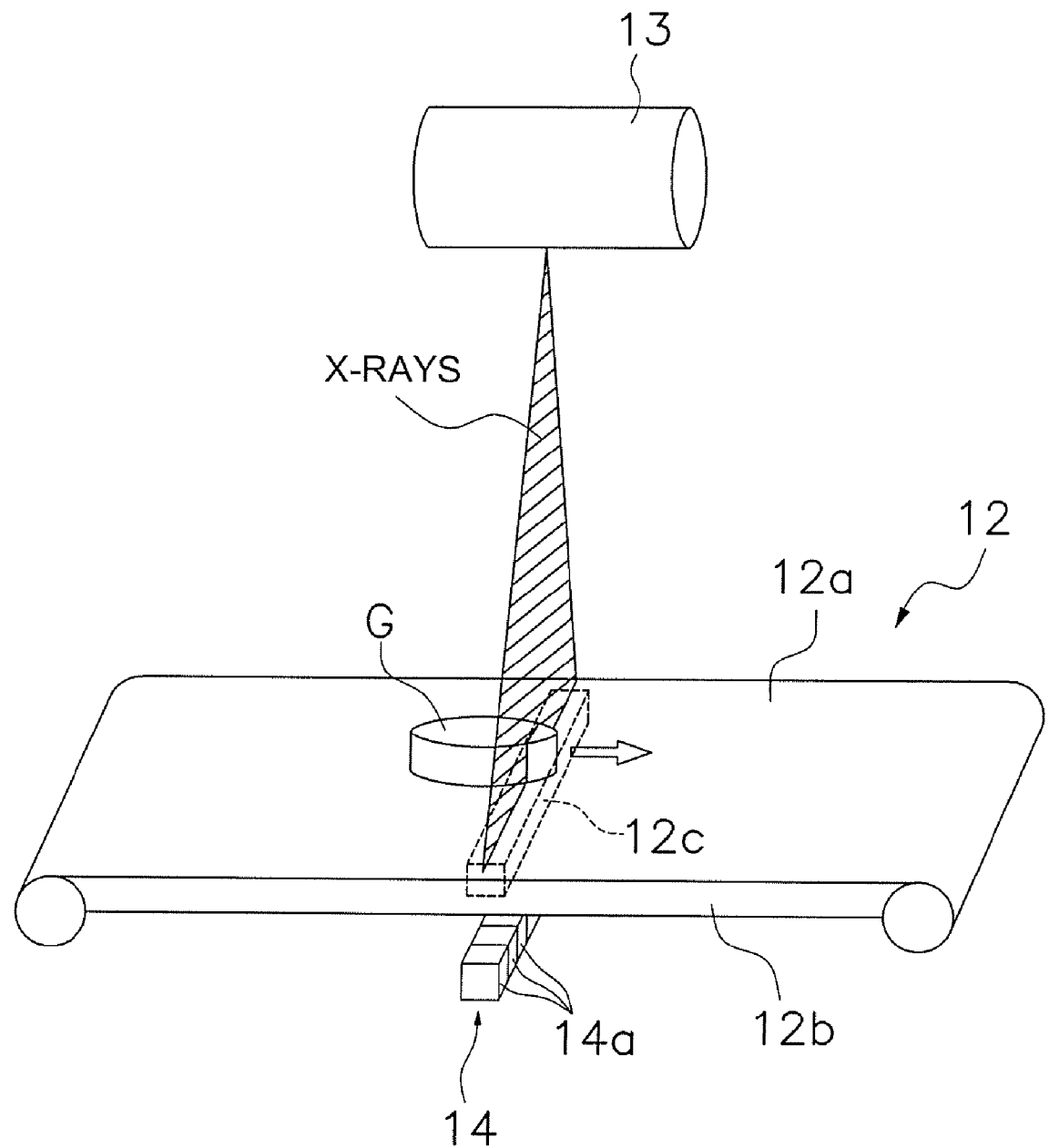
F I G. 3

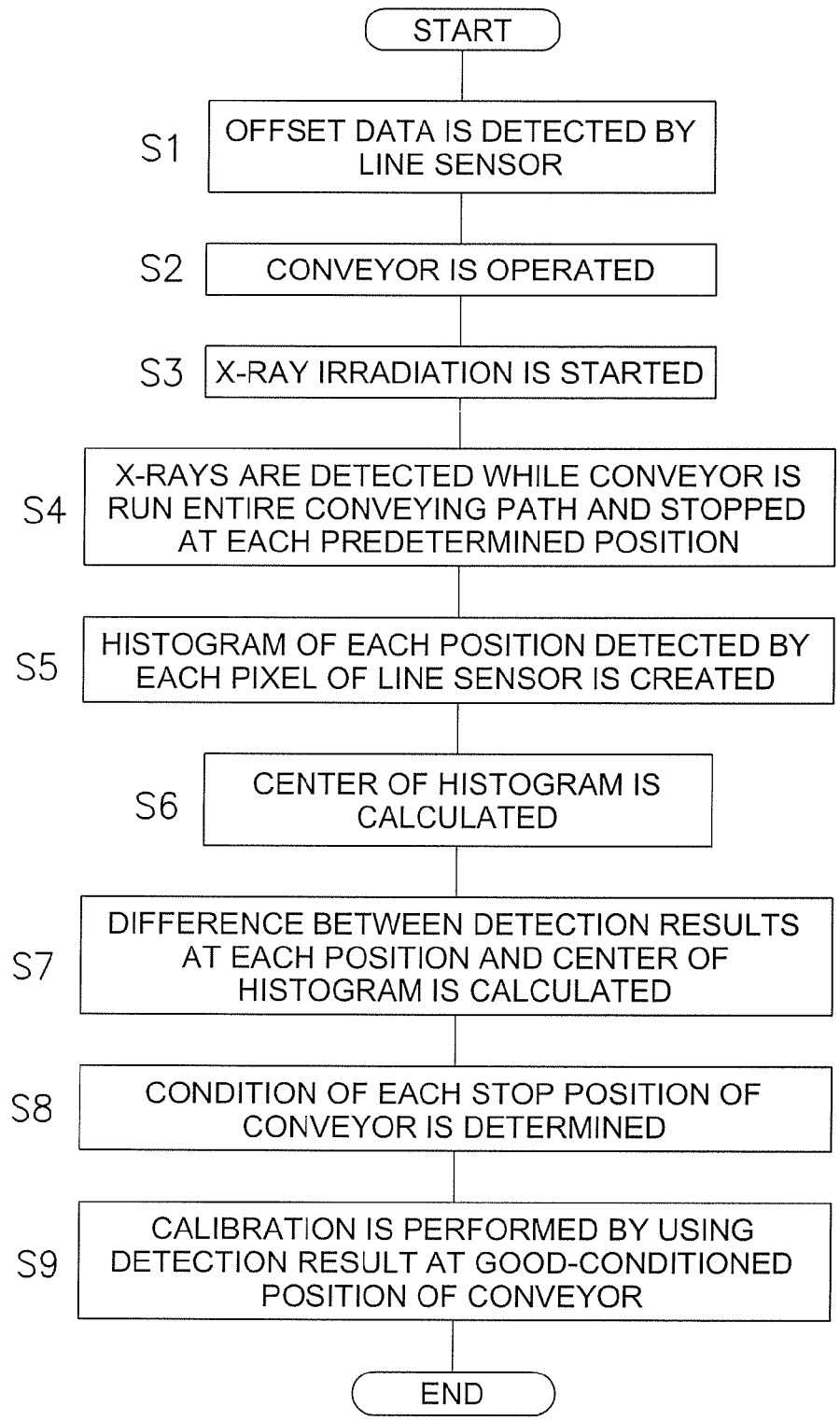
F I G. 7

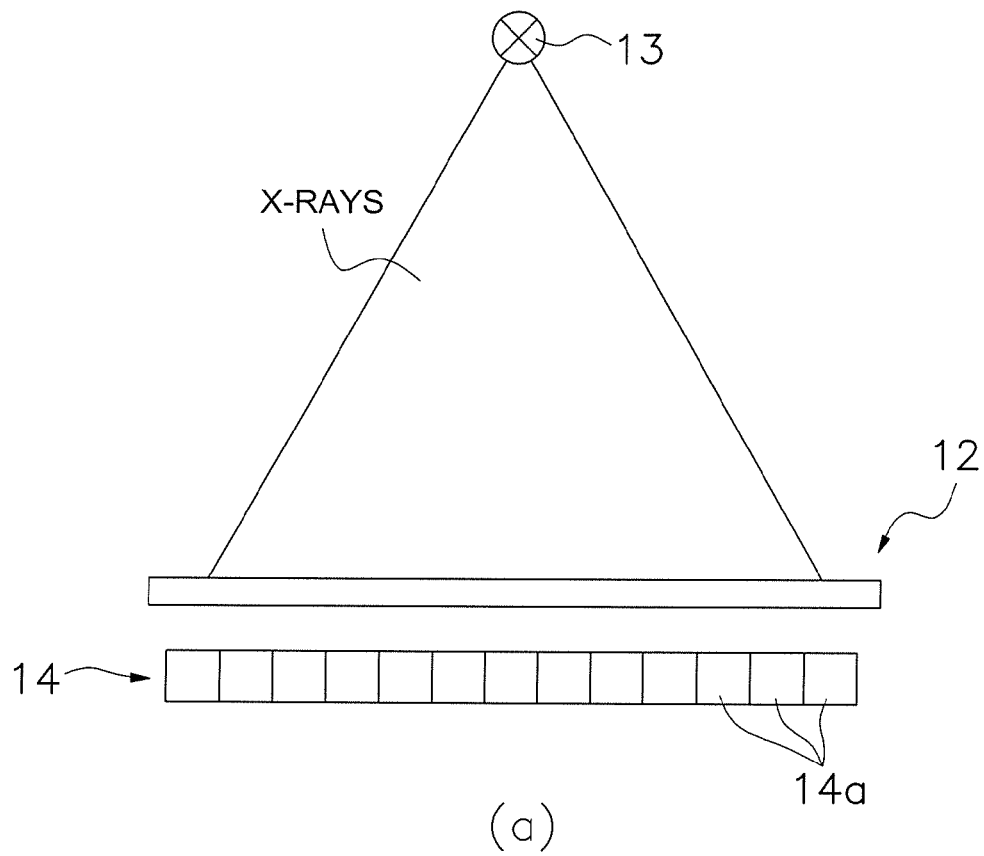
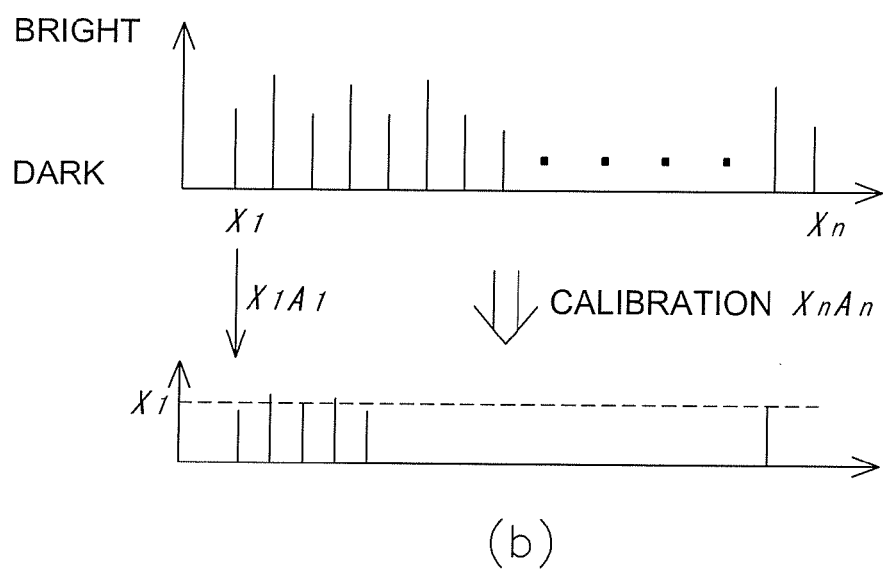
FIG. 8

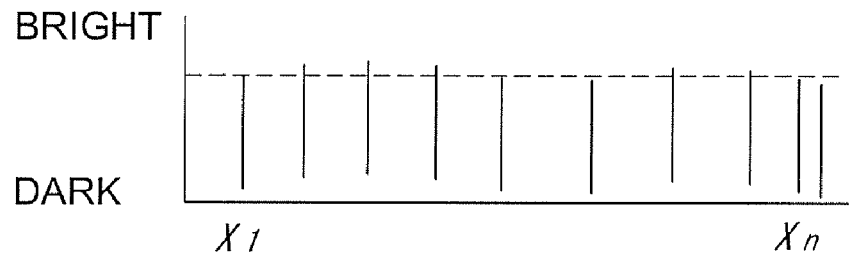
(a) NORMAL POSITION
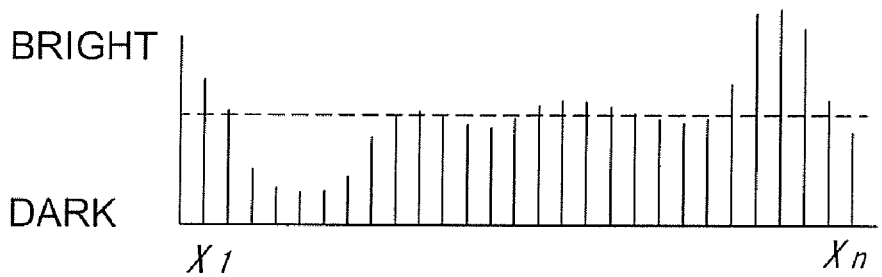
(b) DUST, DIRT, DETERIORATED PORTIONS EXIST
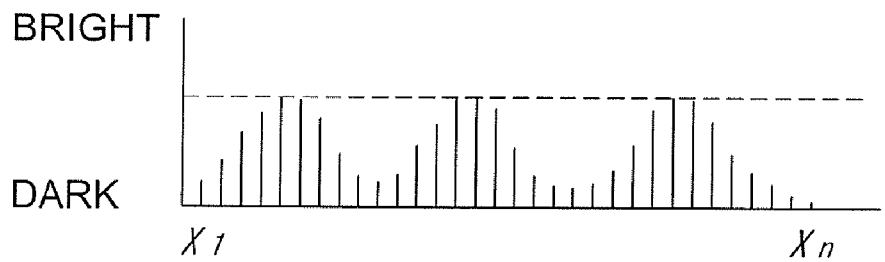
(c) FINGER JOINT
F I G. 9

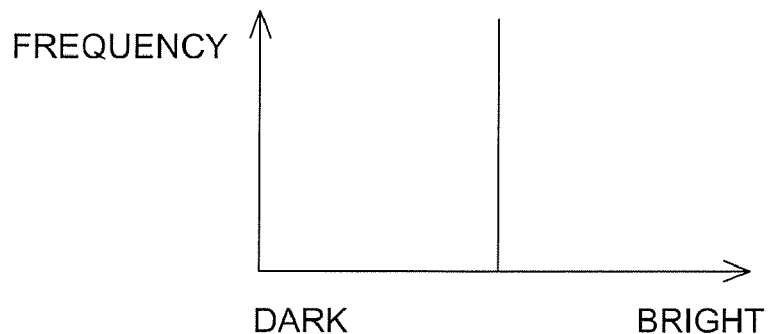
(a) NORMAL POSITION
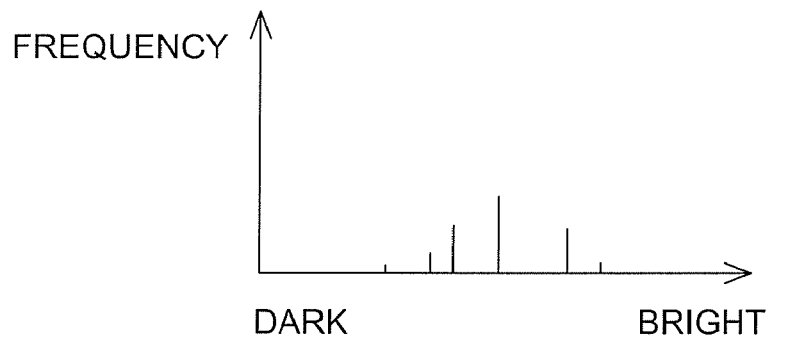
(b) DUST, DIRT, DETERIORATED PORTIONS EXIST
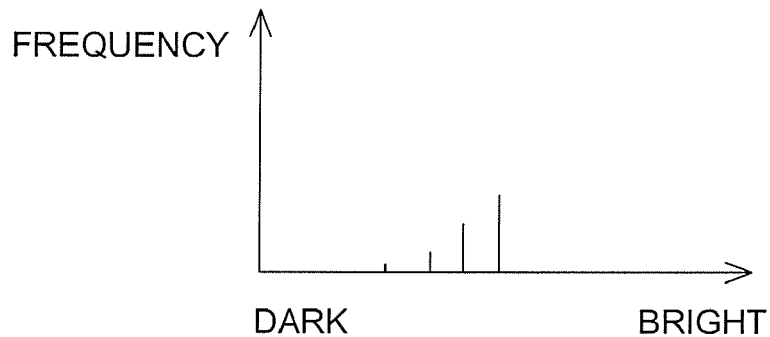
(c) FINGER JOINT
F I G. 1 0

X-RAY INSPECTION APPARATUS AND X-RAY INSPECTION PROGRAM

CROSS-REFERENCE TO RELATED APPLICATIONS

This national phase application claims priority to Japanese Patent Application No. 2006-200283 filed on Jul. 24, 2006. The entire disclosure of Japanese Patent Application No. 2006-200283 is hereby incorporated herein by reference.

TECHNICAL FIELD

The present invention relates to an X-ray inspection apparatus and an X-ray inspection program which irradiate an object to be inspected with X-rays in order to inspect the object.

BACKGROUND ART

Conventionally, on a production line for products such as foods, a defect inspection is performed by using an X-ray inspection apparatus in order to prevent the shipment of defective products, if any, that are contaminated with foreign matter or cracked. Such an X-ray inspection apparatus irradiates target objects being continuously conveyed by a transport conveyor with X-rays. The transmittance state of those X-rays is detected by an X-ray receiving unit, and a determination is made as to whether each target object is contaminated with foreign matter, whether it has cracks, whether there is a shortage in the number of items it contains, and the like.

For example, Japanese Laid-Open Patent Application Publication No. 10-339707 discloses an X-ray diffraction apparatus (X-ray inspection apparatus), in which, for the intensity curve and the intensity level with respect to the angle of the background data, the apparatus determines an intensity curve based on the measurement data of a standard sample, adjusts the level of the intensity curve based on the intensity level, and thereby can obtain adequate background data independent of the object being measured.

DISCLOSURE OF THE INVENTION

However, the above conventional X-ray inspection apparatus has problems, as described below.

Specifically, typically, this type of X-ray inspection apparatus performs a calibration to determine the offset and range of the output of the line sensor. Accordingly, by compensating the sensitivity of X-ray detection by each line sensor through the calibration, it is possible to accurately detect X-rays transmitted through an object to be inspected and highly precisely inspect the object for foreign matter contamination and the like.

It is possible with the X-ray inspection apparatus disclosed in the publication above to obtain adequate background data independent of the object being measured by removing the background image from the measurement data. However, when a transport conveyor that conveys products to be inspected becomes deteriorated or damaged or when a transport conveyor joined with finger joints, for example, is used, X-rays are absorbed in such deteriorated portions, damaged portions, and joint portions. Therefore, the output of the line sensor in such portions becomes smaller than that in non-deteriorated portions and the like (see FIGS. 9(b) and (c)). Accordingly, when the target objects are inspected after a calibration is performed based on positions including such deteriorated portions as the reference, the amount of X-rays detected in the non-deteriorated portions and the like becomes greater than necessary and an X-ray image created based on such detection data becomes too bright. Consequently, an appropriate X-ray image may not be obtained and thus the target object may not be accurately inspected.

Therefore, it is an object of the present invention to provide an X-ray inspection apparatus and an X-ray inspection program capable of accurately inspecting a target object through a highly precise calibration regardless of the condition of a transport conveyor.

An X-ray inspection apparatus according to a first aspect of the present invention is an X-ray inspection apparatus that detects X-rays irradiated to and transmitted through a target object in order to inspect the target object. The X-ray inspection apparatus includes a transport conveyor, an X-ray irradiation unit, a line sensor, a determination unit, and a calibrating unit. The transport conveyor conveys the target object in a predetermined direction. The X-ray irradiation unit irradiates the target object conveyed by the transport conveyor with X-rays. The line sensor includes a plurality of pixels configured to detect X-rays irradiated from the X-ray irradiation unit and transmitted through the transport conveyor at a plurality of prescribed positions of the transport conveyor in a state in which the target object is not placed on the transport conveyor. Based on detection results obtained by the line sensor obtained at each of the prescribed positions of the transport conveyor, the determination unit is configured to determine whether each of the prescribed positions of the transport conveyor is an appropriate position for calibrating the line sensor. The calibrating unit is configured to calibrate the line sensor based on detection results obtained by the line sensor at the position that is determined by the determination unit to be an appropriate position for calibrating the line sensor.

Here, with the X-ray inspection apparatus that detects the X-rays used to irradiate the target object being conveyed and transmitted therethrough via the transport conveyor in order to inspect for contamination of foreign matter and the like contained in the target object, the transport conveyor for conveying the target object is stopped several times in a state in which the target object is not placed thereon and the X-rays are detected at each stop position, when performing the calibration of the plurality of pixels in the line sensor which detect the X-rays. Then, according to the detection results at these several stop positions, a stop position where the difference in the detection results by each pixel is equal to or greater than a predetermined value is determined to be an inappropriate position for the calibration; whereas a stop position where the difference is smaller than a predetermined value is determined to be an appropriate position for the calibration. Subsequently, the calibration is performed based on the detection result obtained by the line sensor through detection at the stop position that is determined to be an appropriate position for the above described calibration.

Here, the above described calibration refers to the actual calibration and also preliminary actions to be taken before performing the calibration, such as accumulation of data for the calibration.

Accordingly, for example, even when some portions of the transport conveyor are locally deteriorated, damaged, or contaminated or even when the transport conveyor includes finger joints and the like, inappropriate stop positions of the transport conveyor for the calibration are specified, and thereby it is possible to perform the calibration at a position other than those inappropriate positions. As a result, it is possible to accurately inspect the target object by preventing a situation where a highly precise calibration cannot be preformed due to the absorption of a portion of the X-rays transmitted through the deteriorated portions, joint portions, and the like.

Note that in the case where the decrease in the amount of X-rays transmitted through the joint portions is constant from the initial stage of the usage, as in the case seen in a finger joint portion, it suffices if data for the calibration is obtained at the initial stage of the usage and if this data is continuously used after the initial stage. On the other hand, as for deterioration and damages of the transport conveyor, by selecting the above described stop position each time the operation is started or the like and by performing the calibration, it is possible to perform an adequate calibration according to the condition of the transport conveyor that changes over time.

An X-ray inspection apparatus according to a second aspect of the present invention is the X-ray inspection apparatus according to the first aspect of the present invention, wherein the line sensor is configured to detect the X-rays at the prescribed positions of the transport conveyor that spread along an entire conveying path of the transport conveyor when obtaining data for determining whether each of the prescribed positions of the transport conveyor is an appropriate position for calibrating the line sensor.

Here, in order to specify inappropriate positions such as deteriorated portions, damaged portions, and the like of the transport conveyor, the line sensor obtains detection data of the transmitted X-rays at each position while the transport conveyor is run the entire conveying path before performing the calibration.

Accordingly, it is possible to specify all inappropriate positions of the transport conveyor. As a result, it is possible to perform a highly precise calibration by performing the calibration at a position other than the inappropriate positions. Further, even when inspection is continuously performed while a plurality of target objects are conveyed, it is possible to perform a highly precise inspection by performing inspection in a manner that avoids the specified inappropriate positions.

An X-ray inspection apparatus according to a third aspect of the present invention is the X-ray inspection apparatus according to the first or second aspect of the present invention, the X-ray inspection further including a histogram creation unit that creates a histogram based on detection data obtained by each of the pixels in the line sensor at each of the prescribed positions of the conveying conveyor. The determination unit is configured to determine whether each of the prescribed positions is an appropriate position for calibrating the line sensor by using a center of the histogram as a reference.

Here, a histogram is created based on the detection data of each position of the transport conveyor, which is obtained by the line sensor. Then, the determination unit uses, as a reference, the mode of the histogram, i.e., the value of the detection data of the most homogenized portion, in order to calculate the difference between the median and the detection data of each position to determine whether each position is an appropriate position or an inappropriate position.

Accordingly, it is possible to easily identify deteriorated portions and damaged portions (inappropriate positions) scattered throughout appropriate positions and accurately specify these inappropriate positions.

An X-ray inspection apparatus according to a fourth aspect of the present invention is the X-ray inspection apparatus according to any one of the first through third aspects of the present invention, wherein the calibrating unit is configured to calibrate the lines sensor by using the detection results obtained by the line sensor for determination by the determination unit.

Here, in order to determine whether each position of the transport conveyor is an appropriate position or an inappropriate position, the calibration is performed based on the detection data of a position determined to be an appropriate position among the detection data obtained by the line sensor at each position.

Accordingly, it is possible to perform the calibration simply if the detection data obtained for identifying appropriate positions and inappropriate positions is obtained just once. This enables improvement of the operation efficiency of the calibration.

An X-ray inspection apparatus according to a fifth aspect of the present invention is the X-ray inspection apparatus according to any one of the first through third aspects of the present invention, wherein the calibrating unit is configured to newly obtain data by the line sensor for the calibration after determination is made by the determination unit.

Here, after determining whether each position of the transport conveyor is an appropriate position or an inappropriate position, the calibration is performed based on the detection data newly obtained by the line sensor at a position determined to be an appropriate position.

Accordingly, because the calibration can be performed based on the detection data newly obtained at the appropriate position, it is possible to perform a higher accurate calibration than before.

An X-ray inspection apparatus according to a sixth aspect of the present invention is the X-ray inspection apparatus according to any one of the first through fifth aspects of the present invention, further including a control unit configured to control the transport conveyor such that the target object is not placed in the position determined to be inappropriate by the determination unit.

Here, for example, when the transport conveyor that includes deteriorated portions and damaged portions approaches a position for receiving the target object, control to accelerate the conveying speed and the like is performed in order to prevent the target object from being placed at such deteriorated portions and the like.

Accordingly, it is possible to prevent the deteriorated portions and damaged portions of the transport conveyor from being included in an X-ray image that is obtained by detecting the X-rays used to irradiate the target object. As a result, it is possible to avoid a situation where the deteriorated portions and the like of the transport conveyor are erroneously determined to be foreign matter contaminating the target object.

An X-ray inspection apparatus according to a seventh aspect of the present invention is the X-ray inspection apparatus according to any one of the first through sixth aspects of the present invention, further including an image creation unit and an image processing unit. The image creation unit creates an X-ray image based on the detection results obtained by the line sensor regarding the X-rays irradiated at the target object. When the target object is inspected, the image processing unit is configured to perform a subtraction process on the X-ray image created by the image creation unit based on detection data obtained by the line sensor for the determination.

Here, by using the detection data obtained at the several positions for specifying inappropriate positions of the transport conveyor, the image processing unit performs the subtraction process on the X-ray image created based on the detection results of the X-rays used to irradiate the target object.

Accordingly, it is possible to eliminate the background from the created X-ray image when inspecting the target object. As a result, it is possible to highly precisely detect foreign matter and the like by eliminating the background from the X-ray image of the target object by using the detection data previously obtained, after a highly accurate calibration is performed.

An X-ray inspection apparatus according to an eighth aspect of the present invention is an X-ray inspection apparatus that detects X-rays arradiated to and transmitted through a target object in order to inspect the target object. The X-ray inspection apparatus includes a transport conveyor, an X-ray irradiation unit, a line sensor, and a calibrating unit. The transport conveyor conveys the target object in a predetermined direction. The X-ray irradiation unit irradiates the target object conveyed by the transport conveyor with X-rays. The line sensor includes at least one pixel configured to detect X-rays emitted from the X-ray irradiation unit. The calibrating unit configured to calculate an average value of an amount of X-rays detected by the pixel in the line sensor at a plurality of positions of the transport conveyor in a state in which the transport conveyor is operated with X-rays from the X-ray irradiation unit without the target object being placed thereon and to calibrate the pixel of the line sensor based on the average value.

Here, X-ray irradiation is performed while the transport conveyor is operated without the target object placed thereon, and the detection data obtained by each pixel during X-ray irradiation is calculated for each pixel as an average value. Then, this average value is compared to the detection data obtained by each pixel during X-ray non-irradiation, and the calibration of the line sensor is performed.

Accordingly, when the positions that include the deterioration and damages of the transport conveyor are part of all of the positions, it is possible to eliminate the effects of deterioration, damages, and the like by calculating an average value of the detection data obtained by each pixel. Accordingly, by performing the calibration of the line sensor based on this average value, it is possible to highly precisely inspect the target object, without being affected by the deterioration and the like of the transport conveyor.

A computer-readable medium according to a ninth aspect of the present invention is encoded with a computer program for detecting X-rays irradiated to and transmitted through a target object. The computer-readable medium includes instructions for determining, based on detection results of an amount of X-rays obtained by a line sensor at each of a plurality of prescribed positions of a transport conveyor in a state in which the target object is not placed on the transport conveyor, whether or not each of the prescribed positions of the transport conveyor is an appropriate position for calibrating the line sensor, and calibrating the line sensor based on detection results obtained by the line sensor at a position determined to be an appropriate position for calibrating the line sensor.

Here, with the X-ray inspection program that detects the X-rays used to irradiate the target object and transmitted therethrough via the transport conveyor in order to inspect for contamination of foreign matter and the like contained in the target object, the transport conveyor for conveying the target object is stopped several times in a state in which the target object is not placed thereon and X-rays are detected at each stop position, when performing the calibration of the plurality of pixels in the line sensor which detect X-rays. Then, according to the detection results at these several stop positions, a stop position where the difference in the detection results by each pixel is equal to or greater than a predetermined value is determined to be an inappropriate position for the calibration; whereas a stop position where the difference is smaller than a predetermined value is determined to be an appropriate position for the calibration. Subsequently, the calibration is performed based on the detection results obtained by the line sensor through detection at the stop position determined to be an appropriate position for the above described calibration.

Here, the above described calibration refers to the actual calibration and also preliminary actions to be taken before performing the calibration, such as accumulation of data for the calibration.

Accordingly, for example, even when some portions of the transport conveyor are locally deteriorated, damaged, or contaminated or even when the transport conveyor includes finger joints and the like, inappropriate stop positions of the transport conveyor for the calibration are specified, and thereby it is possible to perform the calibration at a position other than those inappropriate positions. As a result, it is possible to accurately inspect the target object by preventing a situation where a highly precise calibration cannot be preformed due to the absorption of a portion of the X-rays transmitted through the deteriorated portions, joint portions, and the like.

Note that in the case where the decrease in the amount of X-rays transmitted through the joint portions is constant from the initial stage of the usage, as in the case seen in a finger joint portion, it suffices if data for the calibration is obtained at the initial stage of the usage and if this data is continuously used after the initial stage. On the other hand, as for deterioration and damages of the transport conveyor, by selecting the above described stop position each time the operation is started or the like and performing the calibration, it is possible to perform adequate calibration according to the condition of the transport conveyor that changes over time.

According to the X-ray inspection apparatus of the present invention, it is possible to specify all inappropriate positions of the transport conveyor. As a result, it is possible to perform a highly precise calibration by performing the calibration at a position other than the inappropriate positions.

BRIEF DESCRIPTION OF DRAWINGS

FIG. 1 is an external perspective view of an X-ray inspection apparatus according to an embodiment of the present invention.

FIG. 2 shows the preceding and following structures of the X-ray inspection apparatus.

FIG. 3 is a simplified block diagram of the interior of a shield box of the X-ray inspection apparatus.

FIG. 7 is a flowchart of the flow of a calibration that is performed as an X-ray inspection program is read by the control computer of FIG. 4.

FIGS. 8($a$) and ($b$) are views to describe the principle of a calibration by an X-ray line sensor included in the X-ray inspection apparatus of FIG. 1.

FIGS. 9($a$) to ($c$) are graphs of examples of detection results by the X-ray line sensor, which vary according to the condition of a conveyor.

FIGS. 10($a$) to ($c$) are histograms created based on the graphs of the detection results shown in FIGS. 9($a$) to ($c$).

BEST MODE FOR CARRYING OUT THE INVENTION

Figure 4:
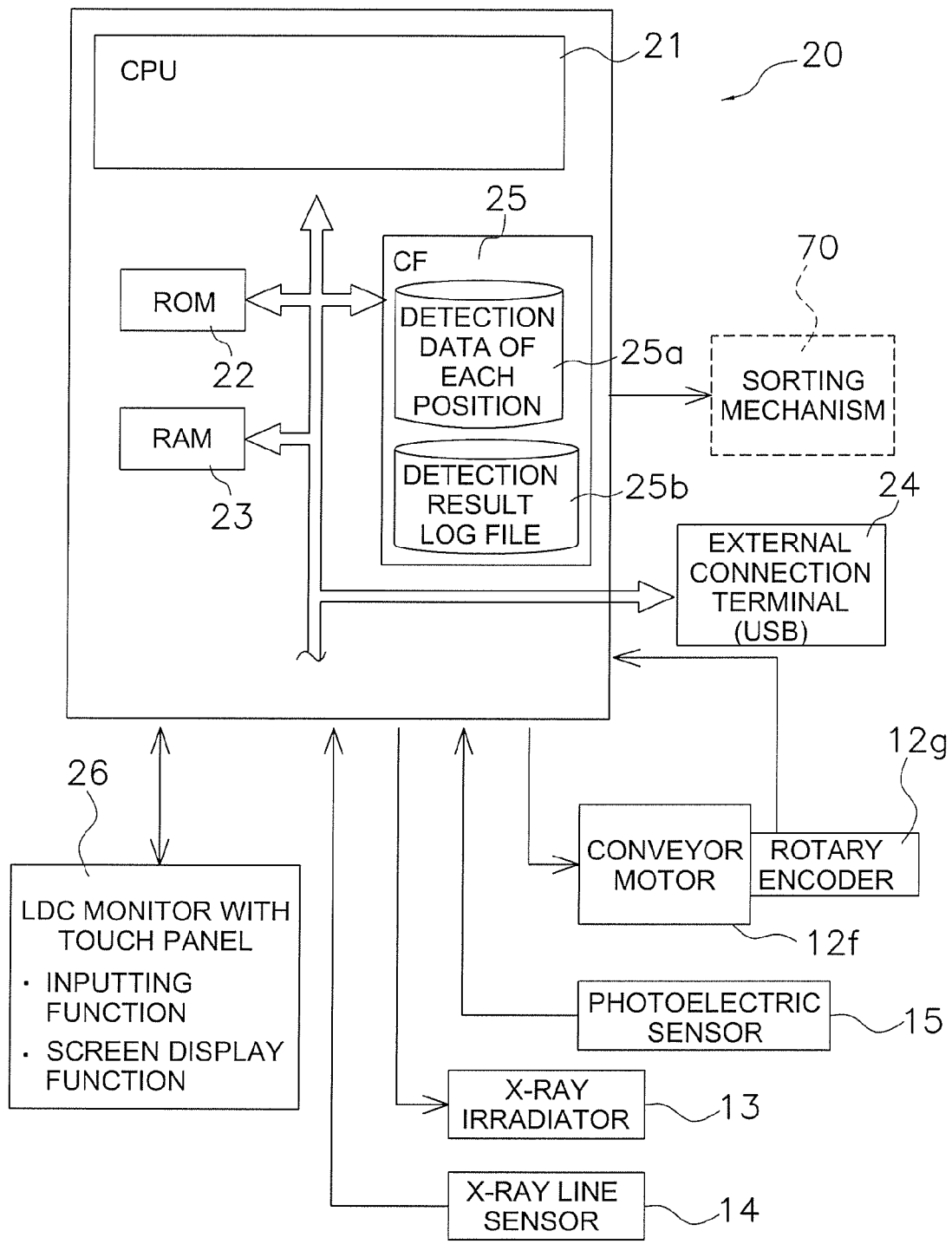
FIG. 4 is a block diagram of a configuration of a control computer installed in the X-ray inspection apparatus of FIG. 1.

An X-ray inspection apparatus 10 according to an embodiment of the present invention is described below with reference to FIG. 1 through FIG. 10.

Overall Structure of X-Ray Inspection Apparatus 10

As shown in FIG. 1, the X-ray inspection apparatus 10 of the present embodiment is one of the apparatuses that perform a quality inspection on a production line for products such as foods. The X-ray inspection apparatus 10 irradiates products being continuously conveyed with X-rays and performs an inspection to determine whether each product is contaminated with foreign matter, based on the amount of X-rays transmitted through the product.

As shown in FIG. 2, a product G, which is a target object of the X-ray inspection apparatus 10, is carried to the X-ray inspection apparatus 10 by an upstream conveyor 60. It is determined in the X-ray inspection apparatus 10 whether the product G is contaminated with foreign matter. The result of the determination by the X-ray inspection apparatus 10 is sent to a sorting mechanism 70, which is disposed on the downstream side of the X-ray inspection apparatus 10. If it is determined in the X-ray inspection apparatus 10 that the product G is a conforming product, then the sorting mechanism 70 sends the product G, as is, to a line conveyor 80, which is the regular conveyor. On the other hand, if it is determined in the X-ray inspection apparatus 10 that the product G is a defective product, then an arm 70a, in which a downstream side end thereof is a rotary shaft, swings so as to block a conveying path. Accordingly, the product G that was determined to be a defective product can be collected by a defective product collection box 90, which is disposed at a position out of the conveying path.

As shown in FIG. 1, the X-ray inspection apparatus 10 mainly includes a shield box 11, a conveyor (transport conveyor) 12, a shielding curtain 16, and a monitor (display apparatus) 26 equipped with a touch panel function. Furthermore, as shown in FIG. 3, the interior of the X-ray inspection apparatus 10 includes an X-ray irradiator (X-ray irradiating unit) 13, an X-ray line sensor 14 (line sensor), and a control computer (determination unit, calibrating unit, histogram creation unit, control unit, image creation unit, image processing unit) 20 (see FIG. 4).

Shield Box 11

The shield box 11 has openings 11a at the entrance side and the exit side surfaces of the shield box 11 in order to carry in and out the product G The shield box 11 houses the conveyor 12, the X-ray irradiator 13, the X-ray line sensor 14, the control computer 20, and the like.

In addition, as shown in FIG. 1, each opening 11a is blocked by shielding curtains 16 in order to prevent the leakage of X-rays to the outside of the shield box 11. The shield curtains 16 have a curtain portion made of a lead containing rubber, and are pushed aside by the product when it is carried in and out.

In addition to the monitor 26, a key insertion slot, a power supply switch, and the like are disposed at the front upper portion of the shield box 11.

Conveyor 12

The conveyor 12 conveys the product G inside the shield box 11 in a predetermined direction, and is driven by a conveyor motor 12f included in a control block shown in FIG. 4. The conveying speed of the conveyor 12 is finely controlled by the control computer 20 through inverter control of the conveyor motor 12f such that the conveying speed is equal to the set speed that is input by an operator.

In addition, as shown in FIG. 3, the conveyor 12 includes a conveyor belt 12a and a conveyor frame 12b, and is removably attached to the shield box 11. Accordingly, when inspecting foods and the like, it is possible to remove and clean the conveyor frequently in order to maintain sanitary conditions inside the shield box 11.

The conveyor belt 12a is an endless belt and its inner side is supported by the conveyor frame 12b. The conveyor belt 12a conveys objects placed thereon in a predetermined direction by being rotated by the driving force of the conveyor motor 12f.

In addition to supporting the endless conveyor belt 12a from the inner side thereof, as shown in FIG. 3, the conveyor frame 12b has an opening 12c, whose opening is long in a direction perpendicular to the conveying direction, at a position facing the surface of the inner side of the conveyor belt 12a. The opening 12c is formed in the conveyor frame 12b on a line that connects the X-ray irradiator 13 and the X-ray line sensor 14. In other words, the opening 12c is formed in the conveyor frame 12b in an area irradiated with X-rays from the X-ray irradiator 13 such that the conveyor frame 12b does not block the X-rays transmitted through the product G.

X-Ray Irradiator 13

As shown in FIG. 3, the X-ray irradiator 13 is disposed above the conveyor 12 and irradiates the X-ray line sensor (line sensor) 14 disposed below the conveyor 12 with X-rays in a fan shape (see the diagonally lined portion in FIG. 3) through the opening 12c formed in the conveyor frame 12b.

X-Ray Line Sensor 14

Figure 5:
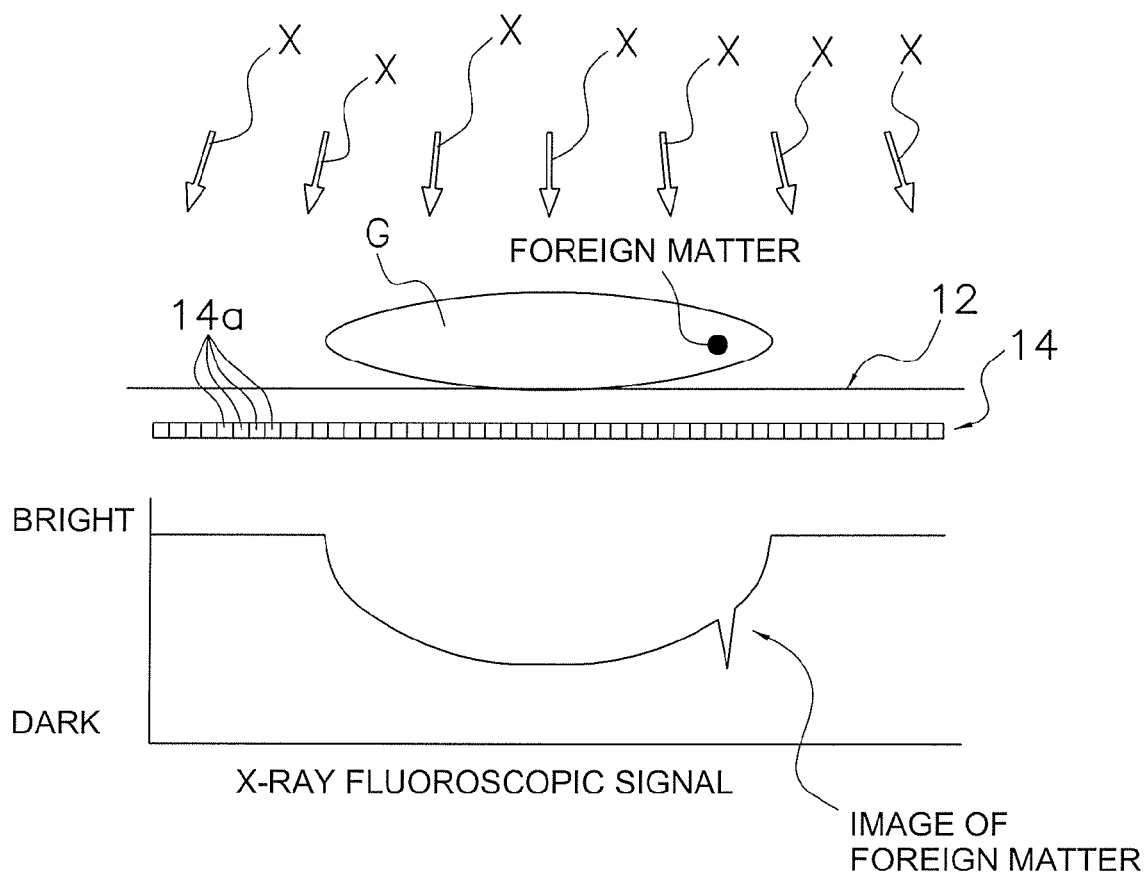
FIG. 5 is a schematic view of the principle of X-ray inspection by the X-ray inspection apparatus of FIG. 1.

The X-ray line sensor 14 is disposed below the conveyor 12 (the opening 12c), and detects the X-rays transmitted through the product G and the conveyor belt 12a. As shown in FIGS. 3 and 5, the X-ray line sensor 14 includes a plurality of pixels 14a horizontally disposed on a straight line oriented orthogonal to the conveying direction of the conveyor 12.

In addition, in a state in which the product G is irradiated with the X-rays in the X-ray inspection apparatus 10, as shown in FIG. 5, the amount of X-rays detected by each pixel 14a constituting the X-ray line sensor 14 at that time is such that the amount detected by the pixel 14a of a portion corresponding to foreign matter is smaller compared to that detected in the surrounding area. Further, when the conveyor belt 12a and the like of the conveyor 12 that conveys the product G include dust, dirt, deteriorated portions, and the like, or when the conveyor 12 includes a finger joint, the detection results by the X-ray line sensor 14 vary as shown in FIGS. 9(b) and (c), compared to a normal state shown in FIG. 9(a).

Further, because errors exist in the sensitivity among the pixels 14a in the X-ray line sensor 14 depending on their detection characteristics, a calibration to eliminate such errors in the sensitivity is performed in accordance with the X-ray inspection program (described later). Note that a method to perform the calibration of each pixel 14a in this embodiment is described later in detail.

Monitor 26

The monitor 26 is a liquid crystal display with a full dot display. In addition, the monitor 26 has a touch panel function and displays screens that prompt the input of parameters related to initial settings and failure determination.

In addition, the monitor 26 displays an X-ray image after image processing (described later) has been performed. This allows the user to visually perceive the presence, location, size, and the like of foreign matter contained in the product G.

Further, the monitor 26 displays X-ray images before and after correction of a dark line that is formed in the X-ray image when the amount of X-ray irradiation becomes unstable (described later), and the monitor 26 also issues warning that inspection cannot be performed because the amount of irradiation by the X-ray irradiator 13 is unstable.

Control Computer 20

The control computer 20 performs, in a CPU 21, an image processing routine, an inspection determination processing routine, and the like included in a control program. In addition, the control computer 20 stores and accumulates X-ray images corresponding to defective products, determination results, correction data of X-ray images, and the like in a memory unit such as a CF (Compact Flash: trademark) 25 and the like.

As a specific configuration, as shown in FIG. 4, the control computer 20 is installed with the CPU 21, and also with a ROM 22, a RAM 23, and the CF 25 as main memory units, which are controlled by the CPU 21. The CF 25 stores detection data 25a of each position of the conveyor 12 to be used for determining whether each position is appropriate for performing the calibration (described later); a detection result log file 25b based on the detection data 25a; correction data for correcting an X-ray image which stores portions (pixels 14a) specified as the background and brightness values of such portions and the like; an inspection result log file that stores inspection images and inspection results; and the like.

In addition, the control computer 20 includes a display control circuit that controls the display of data on the monitor 26; a key input circuit that receives the key input data from the touch panel of the monitor 26; an I/O port that controls the printing of data on a printer (not shown) and the like; a USB 24 that serves as an external connection terminal; and the like.

Further, the CPU 21, the ROM 22, the RAM 23, the CF 25, and the like are mutually connected via bus lines, such as an address bus and a data bus.

Further, the control computer 20 is connected to the conveyor motor 12f, a rotary encoder 12g, the X-ray irradiator 13, the X-ray line sensor 14, a photoelectric sensor 15, and the like.

The rotary encoder 12g is mounted to the conveyor motor 12f. The rotary encoder 12g detects the conveying speed of the conveyor 12 and sends the result to the control computer 20.

The photoelectric sensor 15 is a synchronization sensor for detecting the timing at which the product G, which is the target object, comes to the position of the X-ray line sensor 14, and includes a pair of a light projecting device and a light receiving device, which are disposed so as to sandwich the conveyor.

Figure 6:
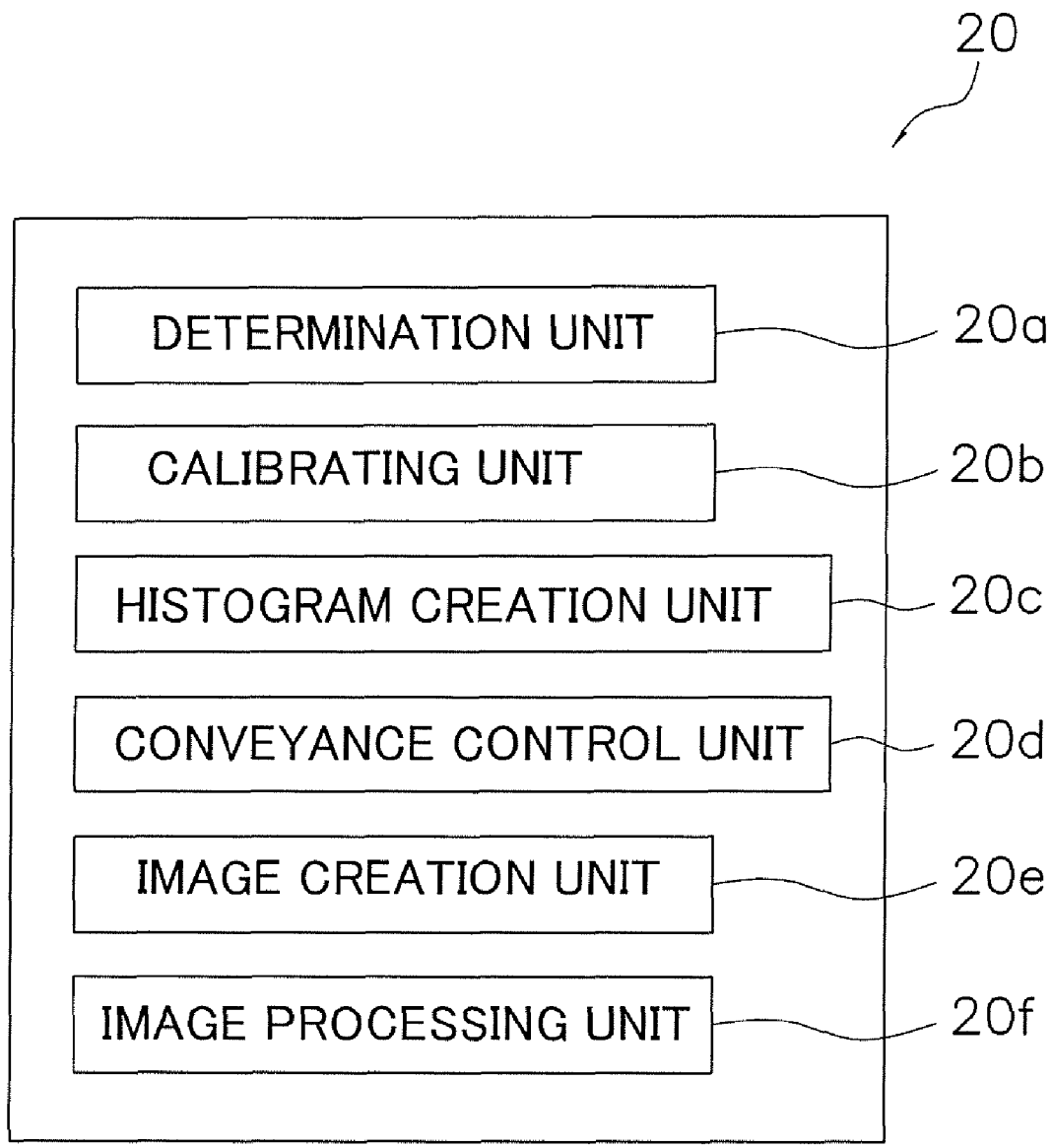
FIG. 6 is a block diagram of a function block formed in the control computer of FIG. 4.

In this embodiment, as the CPU 21 reads in an X-ray inspection program stored in the memory unit such as the ROM 22, RAM 23, or the like, in the control computer 20, as shown in FIG. 6, a function block is formed which includes a determination unit 20a, a calibrating unit 20b, a histogram creation unit 20c, a conveyance control unit (control unit) 20d, an image creation unit 20e, and an image processing unit 20f.

In accordance with the X-ray inspection program (described later), the determination unit 20a determines whether the condition of each position of the conveyor 12 is appropriate for performing the calibration.

The calibrating unit 20b performs the calibration of each pixel 14a in the X-ray line sensor 14 at a position of the conveyor 12 determined by the above described determination unit 20a to be an appropriate position for performing the calibration. Specifically, as shown in FIG. 8(a), each pixel 14a in the X-ray line sensor 14 detects X-rays used to irradiate the conveyor 12 without the product G placed thereon, and the data obtained through the detection is homogenized as shown in FIG. 8(b). By performing this type of calibration, it is possible to correct the errors in the sensitivity that varies in each pixel 14a and to highly precisely inspect the product G.

For the determination as to whether the condition of each position of the conveyor 12 is appropriate for performing the calibration in accordance with the X-ray inspection program (described later), the histogram creation unit 20c creates histograms (see FIGS. 10(a) to (c)) of the detection results obtained by each pixel 14a at each position.

The conveyance control unit 20d is a device that controls the conveyance speed of the conveyor 12, the timing at which the conveyance is started, stopped, and the like. The conveyance control unit 20d controls the conveyor 12 such that the product G is conveyed in a manner that avoids the positions that include deterioration, damages, and the like, which are determined to be inappropriate for performing the calibration, based on the detection results performed in accordance with the X-ray inspection program (described later).

The image creation unit 20e creates an X-ray image to be used for inspecting foreign matter contamination, based on the detection results by each pixel 14a in the X-ray line sensor 14 shown in FIG. 5.

The image processing unit 20f removes the background from the X-ray image created by the image creation unit 20e, reflects the results of the calibration, and performs image processing to make foreign matter to be easily found. Note that in this embodiment, when inspection for foreign matter contamination is performed by detecting the X-rays used to irradiate the product G placed on the conveyor 12 after the calibration is performed based on the detection result by the above described determination unit 20a, the background can be removed from the X-ray image by the above described image processing unit 20f by using the detection results obtained for the determination as to whether each position of the conveyor 12 is appropriate for performing the calibration (described later).

Determination of Condition of Each Position of Conveyor 12 by Control Computer 20

In this embodiment, in accordance with the flow shown in FIG. 7 which is performed by the CPU 21 by reading in the X-ray inspection program, the above described control computer 20 determines the condition of each stop position of the conveyor 12, and thereafter a calibration of the errors in the sensitivity of each pixel 14a in the X-ray line sensor 14 is performed.

In other words, in step S1, the offset data of each pixel is obtained by the X-ray line sensor 14 in a state without the product G placed on the conveyor 12 and without X-ray irradiation.

Next, in step S2, the conveyor 12 is operated in a state without the product G placed thereon.

Next, in step S3, the X-ray irradiator 13 irradiates the conveyor 12 with X-rays in a state without the product G placed thereon.

Next, in step S4, X-rays are detected by the X-ray line sensor 14 while stopping the conveyor 12 at several prescribed positions, and stops the operation of the conveyor 12 just after the conveyor 12 was run the entire conveying path.

Next, in step S5, based on the detection results obtained by the pixels 14a in the X-ray line sensor 14 at each stop position of the conveyor 12, histograms as shown in FIGS. 10(a) to (c) are created. These histograms indicate the relationship between the brightness corresponding to the detection results at each position of the conveyor 12 and the frequency of the brightness. The histogram in FIG. 10(a) shows a result of a case where the condition of the conveyor 12 is normal and the product G is not placed thereon. The histogram in FIG. 10(b) shows a result in a case where, for example, the conveyor belt 12a and the conveyor frame 12b that constitute the conveyor 12 include dust and deteriorated portions. The histogram in FIG. 10(c) shows a result in a case where the conveyor 12 includes a finger joint. As described above, it is clear from the results shown in FIGS. 10(a) to (c) that when the condition of the conveyor 12 is normal, the detection result in which the brightness is substantially uniform is obtained, and when some portions of the conveyor 12 include dust and deteriorated portions, the brightness varies due to the absorption or transmission of the X-rays in these portions.

Next, in step S6, the center of the histograms created in step S5 is determined. The center of the histogram corresponds to the most frequent value (X-ray detection value) detected by the pixels 14a of the line sensor 14 in all the prescribed stop positions. In other words, the mode of the brightness histogram of every stop position of the conveyor 12 is determined. For example, as shown in FIG. 10(a), when the condition of the conveyor 12 is normal, the portion with the highest frequency is the center of the histogram. However, as shown in FIG. 10(b), when the conveyor 12 includes dust and deteriorated portions, the frequency of darker portions (smaller brightness values) other than the normal portion (normal brightness value) increases, and thus the average of the histogram is shifted to the darker side. In other words, when the deteriorated portions and the like included in the conveyor 12 spread across a wider range, a histogram created based on the detection results obtained by the X-ray line sensor 14 at such stop positions is shifted to the darker side. Thus, when a X-ray detection value in each pixel 14a in this histogram is compared to the mode (the most frequency value) of the histogram which indicates an X-ray detection value in a position where the conveyor 12 is in a normal condition, there is a great difference therebetween in the brightness.

Next, in step S7, the X-ray detection result from each pixel 14a at each position is compared to the center (mode) of the histogram obtained in step S6 in order to calculate the overall difference in each position. Note that the processing here is performed to specify a bright portion having the highest frequency in the histogram as the amount of X-rays transmitted through the conveyor 12 in the normal condition.

Next, in step S8, the condition of each stop position of the conveyor 12 is determined according to whether the difference calculated in step S7 is equal to or greater than a predetermined amount. Specifically, when the difference is equal to or greater than a predetermined amount, the position is determined to be an abnormal portion, and when the difference is smaller than a predetermined amount, the position is determined to be a normal position. Accordingly, when the difference between the detection result corresponding to the center of the histogram and the detection results of actual detection at each position is equal to or greater than a predetermined amount, it is assumed that the range of the deteriorated portions and the like is large. Therefore, by determining such portions as abnormal portions (deterioration and damaged portion), it is possible to easily specify abnormal portions scattered throughout normal portions of the conveyor 12.

Next, in step S9, one of the positions determined to be normal positions in step S8 is selected. Then, the calibration is performed using the detection result data of the actual detection at the position and the offset data obtained in step SI. Accordingly, because there is no need to newly obtain detection data for the calibration, the calibration processing can be efficiently performed.

In this embodiment, as described above, based on the detection results obtained at the several stop positions in a state in which the conveyor 12 is operated without the product G placed thereon, the determination is made as to whether the condition of each stop position of the conveyor 12 is normal. Here, when portions that are not normal (abnormal portions) are included in the conveyor 12, the calibration is performed by using the detection result obtained at the normal portion so as to avoid those abnormal portions.

Accordingly, even when the conveyor 12 includes deteriorated portions and damages and the like, by performing the calibration based on the detection result obtained in a manner that avoids these portions, it is possible to always perform a highly accurate calibration, regardless of the condition of the conveyor 12.

Characteristics of X-Ray Inspection Apparatus 10

(1) As shown in FIG. 3, the X-ray inspection apparatus 10 in this embodiment is a device that detects, by the X-ray line sensor 14, the X-rays used to irradiate the product G placed on the conveyor 12 and transmitted therethrough in order to detect whether the product G is contaminated with foreign matter. When performing the calibration of the plurality of pixels 14a in the X-ray line sensor 14, a position of the conveyor 12 which is appropriate for the calibration is searched by various control blocks (see FIG. 6) formed in the control computer 20 installed in the X-ray inspection apparatus 10, and the calibration is performed based on the result detected by the X-ray line sensor 14 at the position.

Specifically as shown in FIG. 7, based on the detection results obtained through detection at each stop position of the conveyor 12, the determination unit 20a shown in FIG. 6 determines whether each position of the conveyor 12 is in good condition. Thereafter, the calibrating unit 20b performs the calibration by using the detection result obtained at a good-conditioned position of the conveyor 12.

Typically, when the surface conveyor belt and the like constituting the conveyor are deteriorated, X-rays are absorbed in those portions or the amount of transmitted X-rays increases, and thus a variation, other than the variation in the sensitivity of each pixel in X-ray line sensor, is generated in the output of the X-ray line sensor disposed below the conveyor belt. Accordingly, in order to perform a normal calibration regardless of the condition of the conveyor, the calibration needs to be performed in a manner that avoids deterioration, damaged portions, and the like of the conveyor.

By so doing, even when a part of the conveyor belt 12*a* and the conveyor frame 12*b* that constitute the conveyor 12 include deterioration and damaged portions, by performing the calibration in a manner that avoids such positions that are not appropriate for the calibration, it is possible to always perform a highly accurate calibration, regardless of the condition of the conveyor 12.

(2) With the X-ray inspection apparatus 10 in this embodiment, when determining the condition of the conveyor 12, as shown in step S4 in FIG. 7, the conveyor 12 is run the entire conveying path and detection data is obtained at each position.

This allows substantially all of the deteriorated portions and the like of the entire conveyor 12 to be recognized, and thus it is possible to take measures by the conveyance control unit 20*d* such as controlling the conveyance of the conveyor 12 such that the product G is not placed on those deteriorated portions and the like.

(3) With the X-ray inspection apparatus 10 in this embodiment, when determining the condition of the conveyor 12, as shown in step S5 in FIG. 7, based on the detection results obtained by each pixel 14*a* in the X-ray line sensor 14 at each stop position, the histogram creation unit 20*c* shown in FIG. 6 creates histograms as shown in FIGS. 10(*a*) to (*c*). Then, as shown in step S6 in FIG. 7, the center of the histogram is determined, and the determination is made as to whether each position is adequate for the calibration, according to the degree of the difference between the brightness at the center of the histograms and the detection results at each stop position.

Accordingly, by identifying the center (mode) of the histogram as the brightness corresponding to the detection result at a normal position, the portion whose brightness is different from the brightness of the normal position can be specified as an inappropriate portion of the conveyor 12 for the calibration. As a result, even when the conveyor 12 includes deterioration and damaged portions, such positions can be easily specified and a highly accurate calibration can be performed at a normal position.

(4) With the X-ray inspection apparatus 10 in this embodiment, as shown in step S9 in FIG. 7, the calibrating unit 20*b* performs the calibration by using the detection results obtained at the positions of the conveyor 12 determined by the determination unit 20*a* to be adequate for the calibration.

Accordingly, a highly accurate calibration processing can be efficiently performed, compared to the case where the processing to determine the condition of the conveyor 12 is performed and then a detection result is newly obtained at a normal position of the conveyor 12 based on the determination result.

(5) With the X-ray inspection apparatus 10 in this embodiment, the conveyance control unit 20*d* shown in FIG. 6 controls the conveyor 12 such that the product G is not placed at the positions of the conveyor 12 determined to be inappropriate for the calibration based on the determination results by the above described determination unit 20*a*.

Accordingly, after performing a highly accurate calibration while preventing the product G from being placed at the deteriorated portions and damaged portions of the conveyor 12, a highly precise inspection for detecting foreign matter can be performed.

(6) With the X-ray inspection apparatus 10 in this embodiment, after the calibration is performed after the condition of the conveyor 12 is determined as described above, X-rays are used to irradiate the product G that is actually being conveyed by the conveyor 12 are detected, and an X-ray image is created by the image creation unit 20*e* (see FIG. 6). When the image processing unit 20*f* (see FIG. 6) removes the background from the X-ray image created by the image creation unit 20*e*, the detection results obtained for the determination described above are used.

In other words, for the above described determination of the condition of the conveyor 12, the detection results obtained in a state in which the conveyor 12 is located at prescribed stop positions are used. Therefore, the average value of these detection results is calculated, and portions corresponding to this average value are removed as the background of the X-ray image. In other words, by calculating the average value of the detection results obtained by the X-ray line sensor 14 at each stop position, it is possible to homogenize the effects of the portions having lower amount of transmitted X-rays and the like, which correspond to the deteriorated portions and the like which exist in some portions among the normal portions of the conveyor 12.

Accordingly, by using the detection data obtained for a highly precise calibration, as is, and by removing the background of the X-ray image, it is possible to highly precisely and efficiently perform the detection of the presence of foreign matter contained in the product G.

OTHER EMBODIMENTS

An embodiment of the present invention is described above, but the present invention is not limited to the above embodiment, and it is understood that variations and modifications may be effected without departing from the spirit and scope of the invention.

(A) The above embodiment is described with an example in which the condition of each position of the conveyor 12 is determined, as shown in FIG. 7, through comparison between the mode of the histogram created based on the detection results obtained by the X-ray line sensor 14 at each stop position of the conveyor 12 and the offset value. However, the present invention is not limited thereto.

Figure 11:
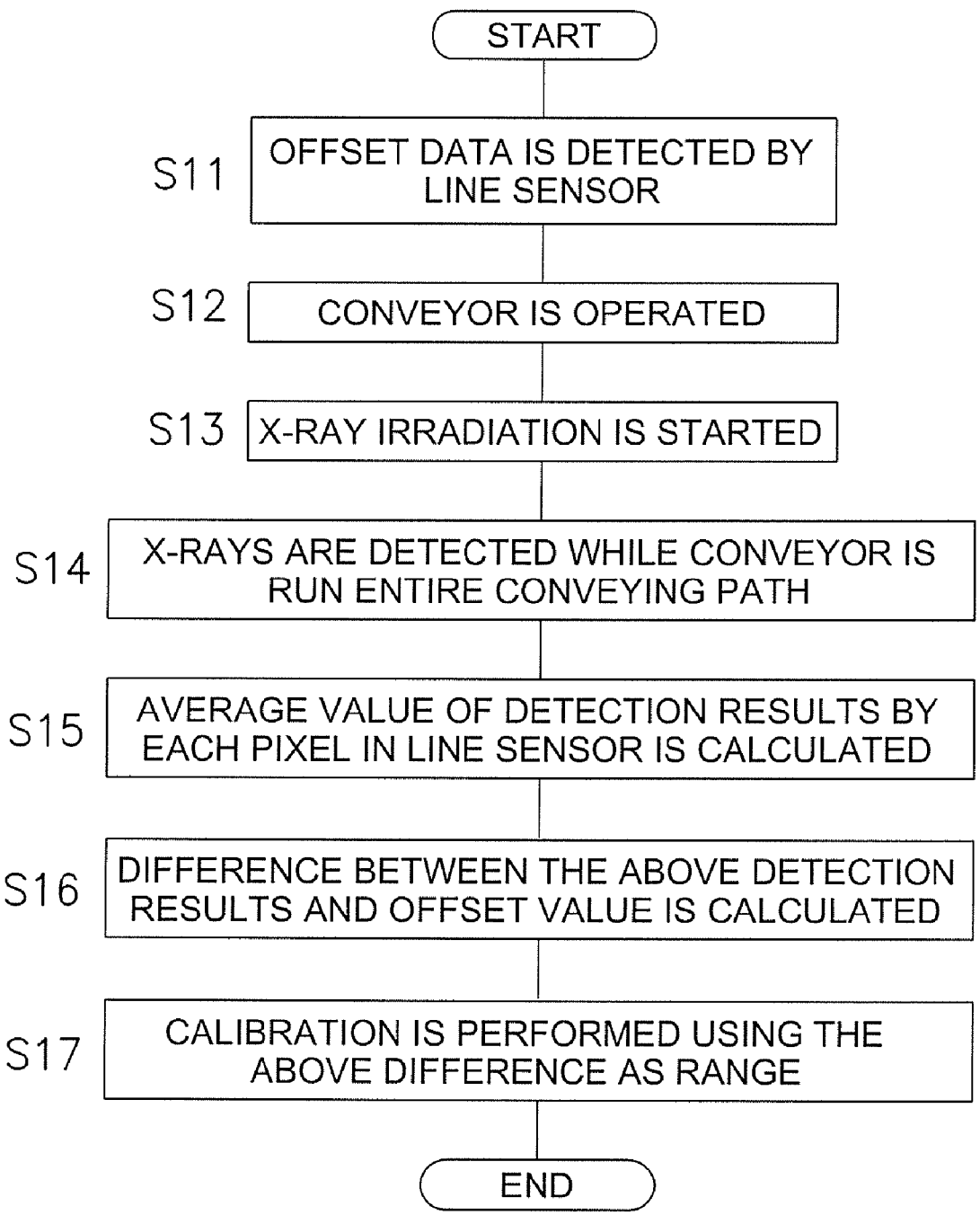
FIG. 11 is a flowchart of the flow of a calibration according to another embodiment of the present invention.

For example, as shown in FIG. 11, in step S11 through step S13, the same processing as in step S1 through step S3 shown in FIG. 7 is performed, and in step S14, X-rays are detected by the X-ray line sensor 14 in a state in which the conveyor 12 is operated. Then, in step S15, an average value of the detection results by each pixel 14*a* is calculated. Thereafter, in step S16, the difference between the average value of the detection results by each pixel 14*a* and the output value (offset value) of each pixel during X-ray non-irradiation is calculated. Then, in step S17, this difference is set as the X-ray detection range of each pixel in the line sensor, and the calibration is performed: this is another possible way.

Also in this case, by calculating the average value of the amount of X-rays detected by each pixel 14*a* while the conveyor 12 is operated, it is possible to homogenize and remove the portions in bad condition due to deterioration and the like of the conveyor belt 12*a* included in the conveyor 12. As a result, it is possible to perform an accurate calibration regardless of the condition of deterioration, damages, and the like of the conveyor 12.

(B) The above embodiment is described with an example in which the detection data obtained at the several positions for specifying appropriate positions of the conveyor 12 is used to perform the calibration. However, the present invention is not limited thereto.

Figure 12:
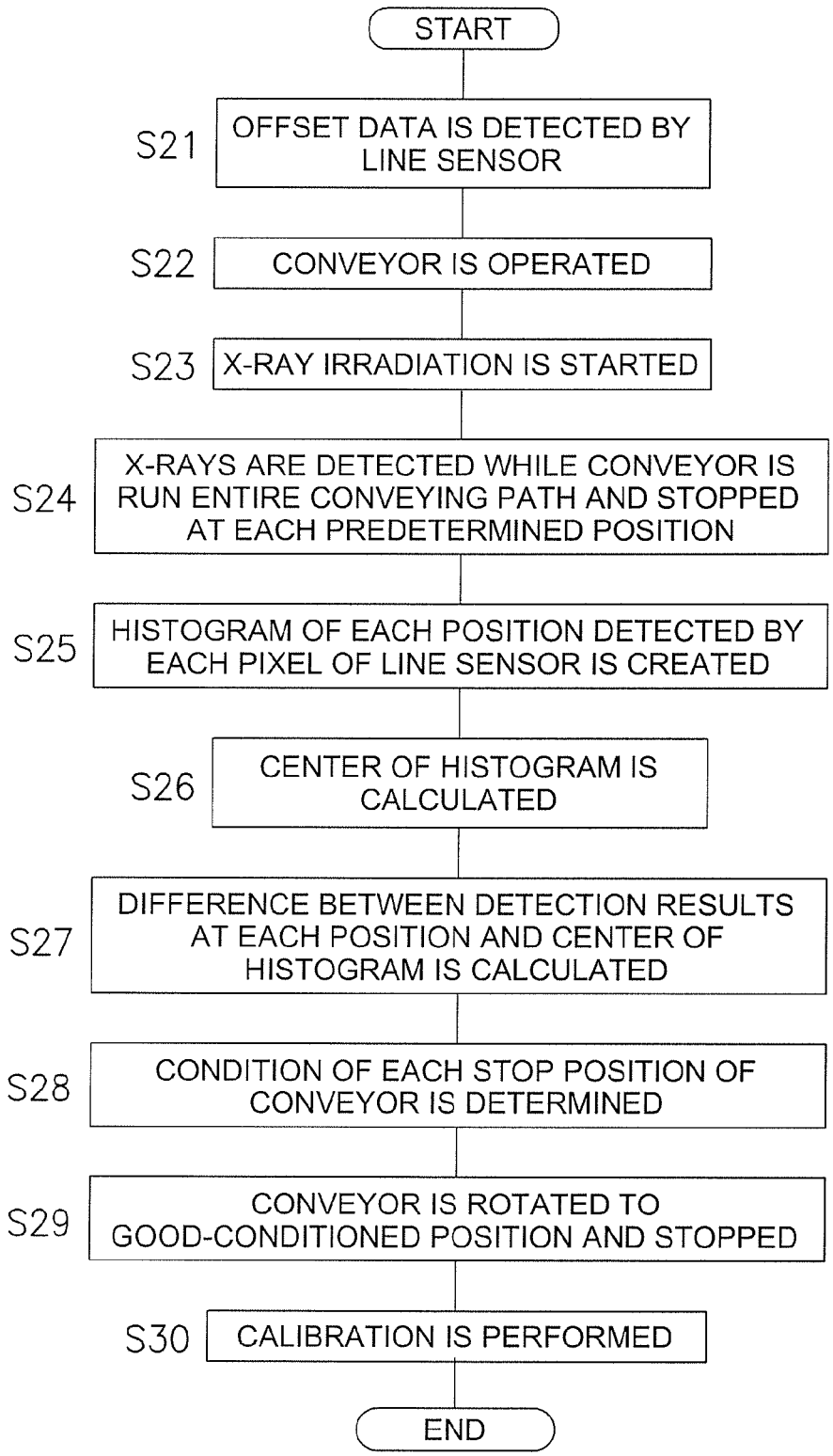
FIG. 12 is a flowchart of the flow of a calibration according to yet another embodiment of the present invention.

For example, as shown in the flowchart in FIG. 12, histograms are created based on detection data obtained by the X-ray line sensor 14 at several stop positions of the conveyor 12, and appropriate positions of the conveyor 12 for calibration are determined (see step S21 through step S28). Thereafter, in step S29, the conveyor 12 is rotated to a position determined to be appropriate (in good condition) for the calibration. Then, in step S30, X-rays are newly detected at the position, and the calibration is performed: this is another possible way.

In this case, the calibration can be performed in a manner that avoids deterioration and damaged portions of the transport conveyor, and thus a highly accurate calibration can be performed as in the above embodiment.

(C) The above embodiment is described with an example in which the conveyor 12 is run the entire conveying path to obtain detection data by the X-ray line sensor 14 at the several positions in order to specify inappropriate positions for the calibration. However, the present invention is not limited thereto.

For example, when the transport conveyor is operated in order to specify the above described inappropriate positions, if appropriate positions are specified based on the detection data obtained at several positions, the operation of the transport conveyor and the obtainment of detection data may be finished at that point.

In this case, because there is no need to obtain the above described detection data on the downstream side at the point when appropriate positions are specified excluding inappropriate positions, the time required for specifying appropriate positions for the calibration is reduced, and a highly accurate calibration can be more efficiently performed.

(D) The above embodiment is described with an example in which the conveyance control unit 20d controls the conveyor 12 such that the product G is not placed at the positions of the conveyor 12 determined to be inappropriate for the calibration. However, the present invention is not limited thereto.

For example, as a method to prevent the product G from being placed at positions of the conveyor 12 determined to be not appropriate for the calibration based on the determination result by the determination unit 20a, an upstream device that conveys the product G to the conveyor 12 may be controlled, instead of controlling the conveyor 12. In this case, by sending the determination result by the determination unit 20a in the control computer 20 to the upstream device, the timing at which the product G is carried into the conveyor 12 is varied, thus preventing the product G from being placed at the inappropriate positions of the conveyor 12.

(E) The above embodiment is described with the X-ray line sensor 14 having 1052 pixels as an example.

However, with the present invention, the number of pixels in the line sensor is not limited thereto. A line sensor having less than 1052 pixels or a line sensor having more than 1052 pixels may be used.

The X-ray inspection apparatus of the illustrated embodiments can achieve the effect that a highly accurate calibration can always be performed regardless of the condition of the transport conveyor, and thus it is widely applicable to various types of X-ray inspection devices installed with transport conveyors.

The invention is:

1. An X-ray inspection apparatus that detects X-rays irradiated to and transmitted through a target object in order to inspect the target object, the X-ray inspection apparatus comprising:
    a transport conveyor configured to convey the target object in a predetermined direction;
    an X-ray irradiation unit configured to irradiate the target object conveyed by the transport conveyor with X-rays;
    a line sensor including a plurality of pixels configured to detect X-rays irradiated from the X-ray irradiation unit and transmitted through the transport conveyor at a plurality of prescribed positions of the transport conveyor in a state in which the target object is not placed on the transport conveyor;
    a determination unit configured to determine, based on an average of X-ray amounts detected by the pixels of the line sensor obtained at each of the prescribed positions of the transport conveyor, whether each of the prescribed positions of the transport conveyor is an appropriate position for calibrating the line sensor; and
    a calibrating unit configured to calibrate the line sensor based on detection results obtained by the line sensor at a position that is determined by the determination unit to be the appropriate position for calibrating the line sensor.

2. The X-ray inspection apparatus according to claim 1, wherein
    the line sensor is configured to detect the X-rays at the prescribed positions of the transport conveyor that spread along an entire conveying path of the transport conveyor when obtaining data for determining whether each of the prescribed positions of the transport conveyor is an appropriate position for calibrating the line sensor.

3. The X-ray inspection apparatus according to claim 1, further comprising
    a histogram creation unit configured to create a histogram based on detection data obtained by each of the pixels in the line sensor at each of the prescribed positions of the transport conveyor,
    the determination unit being configured to determine whether each of the prescribed positions is an appropriate position for calibrating the line sensor by using a center of the histogram as a reference.

4. The X-ray inspection apparatus according to claim 1, wherein
    the calibrating unit is configured to calibrate the line sensor by using the detection results obtained by the line sensor for determination by the determination unit.

5. The X-ray inspection apparatus according to claim 1, wherein
    the calibrating unit is configured to newly obtain data by the line sensor for the calibration after determination is made by the determination unit.

6. The X-ray inspection apparatus according to claim 1, further comprising
    a control unit configured to control the transport conveyor such that the target object is not placed in a position of the target conveyor that is determined to be inappropriate by the determination unit.

7. The X-ray inspection apparatus according to claim 1, further comprising
    an image creation unit configured to create an X-ray image based on the detection results obtained by the line sensor regarding the X-rays irradiated at the target object, and
    an image processing unit configured to perform a subtraction process on the X-ray image created by the image creation unit based on detection data obtained by the line sensor for determination by the determination unit, when the target object is inspected.

8. An X-ray inspection apparatus that detects X-rays irradiated to and transmitted through a target object in order to inspect the target object, the X-ray inspection apparatus comprising:

a transport conveyor configured to convey the target object in a predetermined direction;

an X-ray irradiation unit configured to irradiate the target object conveyed by the transport conveyor with X-rays;

a line sensor including at least one pixel configured to detect X-rays irradiated from the X-ray irradiation unit; and a calibrating unit configured to calculate an average value of an amount of X-rays detected by the pixel in the line sensor at a plurality of positions of the transport conveyor in a state in which the transport conveyor is operated with X-rays emitted from the X-ray irradiation unit without the target object being placed thereon and to calibrate the pixel of the line sensor by setting a difference between the average value and an offset value, which is an output value of the pixel when the X-rays are not irradiated from the X-ray irradiation unit, as a X-ray detection range of the pixel of the line sensor.

9. A computer-readable medium encoded with a computer program for detecting X-rays irradiated to and transmitted through a target object in order to inspect the target object, comprising instructions for:

determining, based on an average of X-ray amounts detected by pixels of a line sensor at each of a plurality of prescribed positions of a transport conveyor in a state in which the target object is not placed on the transport conveyor, whether or not each of the prescribed positions of the transport conveyor is an appropriate position for calibrating the line sensor; and calibrating the line sensor based on detection results obtained by the line sensor at a position determined to be an appropriate position for calibrating the line sensor.

* * * * *